(12) United States Patent
Simnacher et al.

(10) Patent No.: US 8,088,073 B2
(45) Date of Patent: Jan. 3, 2012

(54) DEVICE FOR THE APPLICATION OF ACOUSTIC SHOCK WAVES

(75) Inventors: Erwin Simnacher, Reichenau (DE); Dick van Rijn, Hergatz (DE)

(73) Assignee: SANUWAVE, Inc., Alpharetta, GA (US)

( * ) Notice: Subject to any disclaimer, the term of this patent is extended or adjusted under 35 U.S.C. 154(b) by 266 days.

(21) Appl. No.: 10/952,806

(22) Filed: Sep. 30, 2004

(65) Prior Publication Data

US 2005/0075588 A1    Apr. 7, 2005

(30) Foreign Application Priority Data

Oct. 1, 2003 (EP) .................................... 03022056

(51) Int. Cl.
*A61B 8/14* (2006.01)
(52) U.S. Cl. ........ 600/472; 367/140; 367/147; 367/151; 600/439; 601/2; 601/3; 601/4
(58) Field of Classification Search .................. 600/439, 600/472; 601/2, 3, 4; 367/140, 147, 151
See application file for complete search history.

(56) References Cited

U.S. PATENT DOCUMENTS

| | | | |
|---|---|---|---|
| 4,858,613 A * | 8/1989 | Fry et al. ........................ | 600/439 |
| 4,957,099 A | 9/1990 | Hassler | |
| 4,979,500 A * | 12/1990 | Hassler et al. .................... | 601/4 |
| 4,991,604 A * | 2/1991 | Wurster et al. ................. | 600/439 |
| 5,036,855 A | 8/1991 | Fry et al. | |
| 5,065,740 A | 11/1991 | Itoh | |
| 5,085,206 A * | 2/1992 | Mestas et al. ...................... | 601/4 |
| 5,156,144 A * | 10/1992 | Iwasaki et al. .................... | 601/4 |
| 5,419,335 A * | 5/1995 | Hartmann et al. ............. | 600/472 |
| 6,007,499 A * | 12/1999 | Martin et al. ...................... | 601/3 |
| 6,083,159 A * | 7/2000 | Driscoll et al. ................ | 600/371 |
| 6,361,531 B1 * | 3/2002 | Hissong ........................... | 606/27 |
| 6,432,067 B1 * | 8/2002 | Martin et al. ...................... | 601/2 |
| 2001/0031922 A1 * | 10/2001 | Weng et al. .................... | 600/439 |
| 2004/0006288 A1 * | 1/2004 | Spector et al. .................... | 601/2 |

FOREIGN PATENT DOCUMENTS

DE         3743883 A1    7/1988

* cited by examiner

*Primary Examiner* — Long V. Le
*Assistant Examiner* — Ellsworth Weatherby
(74) *Attorney, Agent, or Firm* — Hunton & Williams LLP

(57) ABSTRACT

A device, in particular a therapy device, for the application of acoustic shock waves aimed at a region to be treated in a human or animal body and comprising a housing with a coupling surface for coupling the shock waves into the body to be treated, a shock wave generating device and a means suitable for focusing the shock waves, in which the shock wave generating device and the means suitable for focusing the shock waves are enclosed in a housing and designed such that they can be moved relative to the coupling surface.

11 Claims, 3 Drawing Sheets

DEVICE FOR THE APPLICATION OF ACOUSTIC SHOCK WAVES

BACKGROUND OF THE INVENTION

The invention relates to a device, in particular a therapy device for the application of acoustic shock waves and comprising a housing with a coupling surface for coupling the shock waves into the body to be treated, a shock wave generating device, and a means suitable for focusing the shock waves.

Therapy devices of this kind for the application of acoustic shock waves are used, for example, for lithotripsy or for human applications in the field of orthopaedics. The therapy device is also used in the field of veterinary medicine.

In this context the region to be treated is located and a necessary number of acoustic shock waves are applied. In this context the region to be treated can be located at varying distances from the surface of the patient's body. This distance depends on:
1) the type of region to be treated (e.g. renal calculi or soft-tissue structures) and
2) the patient's constitution (i.e. obese or not obese).

The penetration depth of the acoustic shock waves is defined by the site of shock wave generation and the geometry of the shock wave focusing device.

For positioning the shock wave focus in the particular regions in the patient's body to be treated, which regions are located at different depths, therapy devices with different fixed or variable penetration depths are required.

It is known from DE 195 09 004 C1 that, in a device of the above-named type, exchangeable coupling attachments, e.g. coupling pads or coupling cushions, are foreseen in order to vary the distance between the shock wave generating device and the coupling surface of the shock waves in the patient's body, whereby the position of the shock wave focus can be adjusted on the region in the patient's body to be treated. It has been noted, however, that the additional coupling surface results in poorer transmission of energy by the shock waves. Furthermore, no infinitely adjustable penetration depths are possible but only predetermined penetration depths corresponding to the thickness of the coupling pad or coupling cushion. In addition, the mounting of the coupling inserts makes the handling of the device more complicated.

A device of the kind mentioned at the beginning, in which various hand-held therapy devices with different penetration depths can be connected in a detachable manner to a supply unit, is known from DE 197 18 511 C2. Here again no infinitely variable adjustment of penetration depth is possible. The therapy heads must be replaced in each case for different applications.

In DE 199 35 724 A1 a therapy device is described in which the coupling membrane provided for coupling the device to the patient has a flexible design and can be moved at various distances from the treatment site via coupling fluid displacement and can be placed on the patient's body. The distance between the shock wave generating device and the coupling surface provided for coupling the shock waves into the body of the patient to be treated is thus variable. Infinitely variable adjustment of the penetration depth of the shock waves in the patient's body is thereby achieved. However, an elastic coupling membrane is required in the above-named device; this membrane is subject to rapid aging owing to the heavy demands placed on it. Furthermore, a compressed air device with a corresponding compressed air line is necessary to control the displacement of coupling fluid. The inconvenient handling as well as the complicated and cost-intensive manufacture due to the additional compressed-air generating device, have proven to be disadvantageous.

A common feature of all of the above-mentioned variants is that either the coupling membrane is moved or additional parts are necessary. This shortens the life cycle of the device and makes handling complicated.

Against the background of the above-mentioned embodiment, the essential thought of the invention is to improve a device of the kind mentioned at the beginning such that it achieves a high flexibility of application as well as fast and simple positioning of the shock wave focus in the therapy region with only a small transmission loss by the shock waves.

BRIEF SUMMARY OF THE INVENTION

The underlying idea of the invention is to provide a device for the application of acoustic shock waves aimed at a region to be treated in a human or animal body, and comprising a housing with at least one coupling surface for coupling the shock waves into the body to be treated, a shock wave generating device, and a means suitable for focusing the shock waves such that the shock wave generating device and the means suitable for focusing the shock waves can be moved in the housing relative to the coupling surface.

The position of the shock wave generating device, together with the means suitable for focusing the shock waves, can be altered in the housing relative to the coupling surface according to the invention. In this context the shock wave generating device—together with the means suitable for focusing the shock waves—is designed, in an advantageous way, in a movable manner on a first axis running from the shock wave generating device through the coupling surface to a shock wave focus created by the means suitable for focusing the shock waves. By means of an axial displacement, in the direction of the coupling surface, of the shock wave generating device together with the means suitable for focusing the shock waves in the device according to the invention, the penetration depth of the shock waves is varied in the patient to be treated and can be adjusted to the region to be treated. The housing with the coupling surface is arranged in a fixed position with respect to the shock wave generating device and the means suitable for focusing the shock waves.

By using the device according to the invention, it is possible to infinitely vary the penetration depth of the shock waves in the patient's body, and thus the depth of the focus, with one and the same device, without employing any accessory parts.

The coupling surface, which is preferably formed by a coupling membrane, does not have to be moved and is thus not subject to any wear or premature aging.

In another embodiment the shock wave generating device is designed in a movable manner, together with the means suitable for focusing the shock waves, on at least a second axis forming an angle with the first axis. This permits—in addition to the positioning of the shock wave focus in a therapy region which is located at varying distances from the coupling surface of the therapy device—a positioning of the shock wave focus on a surface running, for example, vertical to the direction of propagation of the shock waves in the patient's body.

With this design the shock wave focus can be positioned faster in the region to be treated in the patient's body and a larger region in the patient's body can be treated without the necessity of moving the patient, a patient-positioning device or the therapy device. This is advantageous, in particular, in the treatment of orthopaedic disorders. During the treatment of pseudarthroses, in particular, it is advantageous to displace the shock wave focus on three-dimensional axes running along a fracture.

In another advantageous embodiment of the device according to the invention, the shock wave generating device, together with the means suitable for focusing the shock waves, is fastened to a point in the housing and designed in a movable manner such that the shock wave generating device, together with the means suitable for focusing the shock waves, can be tilted around this point. This permits movement of the shock wave focus over an area corresponding to a segment of a circle.

Moreover, the shock wave generating device, together with the means suitable for focusing the shock waves, can be moved in the direction of the coupling surface and tilted in various directions either simultaneously or consecutively. Using the above-described movements, it is possible to move the shock wave focus within a three-dimensional therapy region in the patient's body.

The movement of the shock wave generating device together with the means suitable for focusing the shock waves can be carried out either manually or electromechanically via an electrical drive.

The position of the shock wave generating device, together with the means suitable for focusing the shock waves, on the first axis can be recorded. In this way the penetration depth of the shock waves in the patient's body, as well as the position of the shock wave focus at a distance from the coupling surface, can be determined and displayed to the user. The display can be made by means of a numerical scale on the outside of the housing or by means of an electrical display.

In the embodiment of the device according to the invention in which the movement of the shock wave generating device together with the means suitable for focusing the shock waves is carried out by an electromechanical drive, the revolutions of the drive motor can be recorded, the change in position achieved can be calculated, and the position of the shock wave focus at a distance from the coupling surface can be shown on a display unit on the therapy device.

This permits quick therapeutic positioning of the therapy device on treatment sites located close to the patient's skin.

In another embodiment, moreover, an operator's unit has been provided on the housing of the therapy device for the electromechanical movement of the shock wave generating device along with the means suitable for focusing the shock waves and thus for a positioning of the shock wave focus in the therapy region. The convenient handling of the therapy device has thereby been increased further.

In particular, the movement sequence of the shock wave generating device and the means suitable for focusing the shock waves can be coupled to an imaging system. In this context the movement of the shock wave generating device along with the means suitable for positioning the shock waves in the particular therapy region can preferably be carried out automatically after the region has been located by the imaging system In addition to improved handling and wear resistance, the solution according to the invention results in a distinct increase in the flexibility of the device due to the increased possibilities for use.

In a preferred embodiment, the generation of shock waves by the shock wave generating device is based on the electrohydraulic principle. However, the shock waves can also be generated, for example, by electromagnetic or piezoelectric means.

Focusing is carried out with a reflector, i.e. in a manner that is, in itself, known. Shock waves focussed by reflectors may take the shape of half-shell ellipsoids or paraboloids with various axial constellations. However, acoustic lenses with different focal lengths may also be used for focusing. In addition, half-shell arrangements of electrical membranes or piezocrystal elements with various diameters may be used.

The maximum penetration depth of the shock waves is defined via the various geometric configurations of the means suitable for focusing the shock waves.

BRIEF DESCRIPTION OF THE DRAWING

These and other features, aspects and advantages of the present invention will become better understood with reference to the following description, appended claims, and accompanying drawing, where:

DETAILED DESCRIPTION OF THE INVENTION

Figure 1:
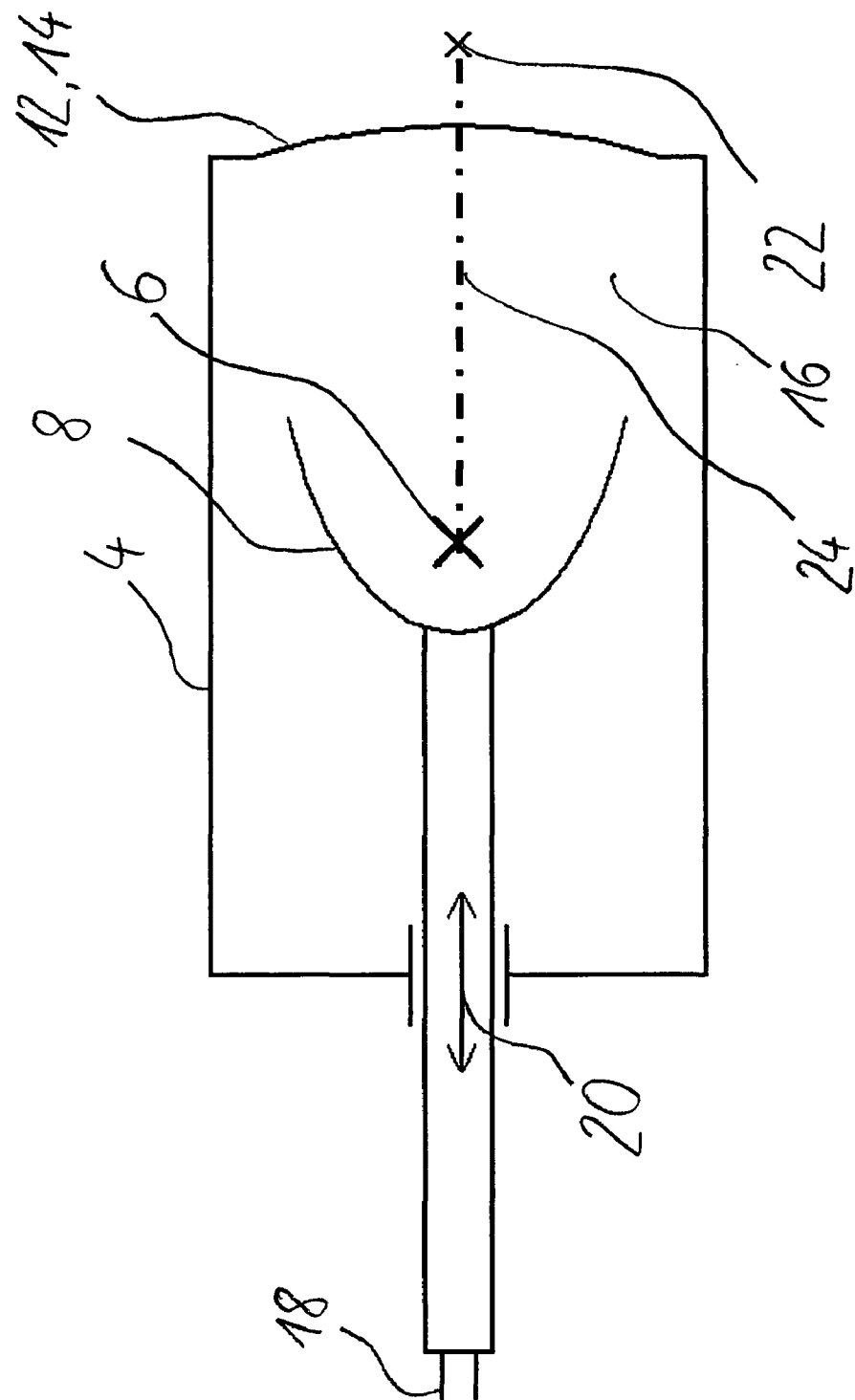
FIG. 1 shows a side view of the device according to the invention in its first preferred embodiment.

The invention summarized above and defined by the enumerated claims may be better understood by referring to the following detailed description, which should be read in conjunction with the accompanying drawing. This detailed description of a particular preferred embodiment, set out below to enable one to practice the invention, is not intended to limit the enumerated claims, but to serve as a particular example thereof. In the drawings the four embodiment examples of the device according to the invention are shown in schematic and simplified form. Equivalent parts are indicated by the same reference numbers.

The schematic presented in FIG. 1 shows a side view of the first embodiment of the device according to the invention. A housing 4 together with a coupling membrane 14 form a closed volume in which a medium 16 suitable for the further transmission of the shock waves is introduced. The coupling membrane 14 forms the coupling surface 12 of the therapy device for coupling the shock waves into the body to be treated.

In the housing 4 there is a shock wave generating device 6, driven by means of at least one supply line 18, and a means suitable for focusing the shock waves 8, referred to in the following as focusing device 8.

The shock wave generating device 6 and the focusing device 8 are arranged jointly in a movable manner on a first axis 24 running from the shock wave focusing device 6 through the coupling membrane 14 to a shock wave focus 22 created by the focusing device 8. An axial movement 20 of the shock wave generating device 6 together with the focusing device 8 takes place with respect to the spatially fixed housing 4 in the direction and opposite to the direction of the coupling surface 12. The distance between the shock wave generating device 6 and the focusing device 8 on the one hand and the coupling surface 12 on the other can be varied. The distance between the shock wave generating device 6 and the shock wave focus 22 is determined by the geometry of the focusing device 8. The penetration depth of shock waves in the patient's body, and thus the position of the shock wave focus 22, are changed by varying the distance between the focusing device 8 and the shock wave generating device 6 on the one hand and the coupling surface 12 on the other.

A movement 20 of the shock wave generating device 6 together with the focusing device 8 in the housing 4 can be carried out manually, electromechanically or hydraulically by means of an electric or hydraulic drive.

In the embodiment depicted, the principle of action of shock wave generating device 6 is based on the electro-hydraulic principle.

In another embodiment, which is not depicted explicitly here, the shock wave generating device 6 and the focusing device 8 interact with a second membrane, thereby applying this principle of action, to form a second closed volume located inside the volume created by housing 4 and the coupling membrane 14. Conducting particles may be introduced into this second volume for the purpose of promoting spark discharge as is known from EP 0 781 447 B1.

Figure 2:
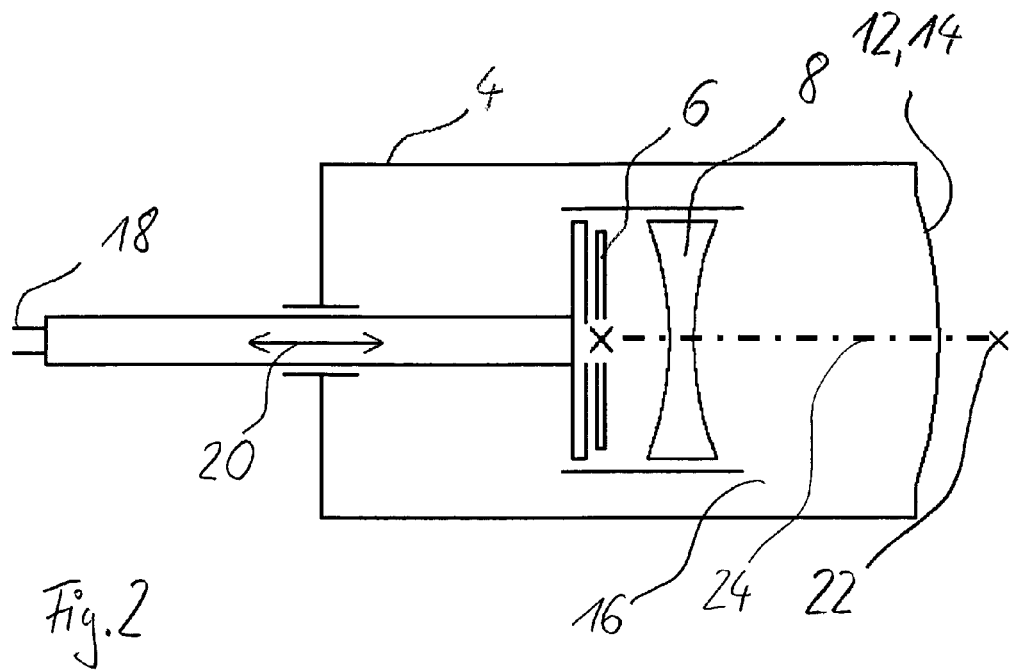
FIG. 2 shows a a side view of the device according to the invention in its second embodiment.
Figure 3:
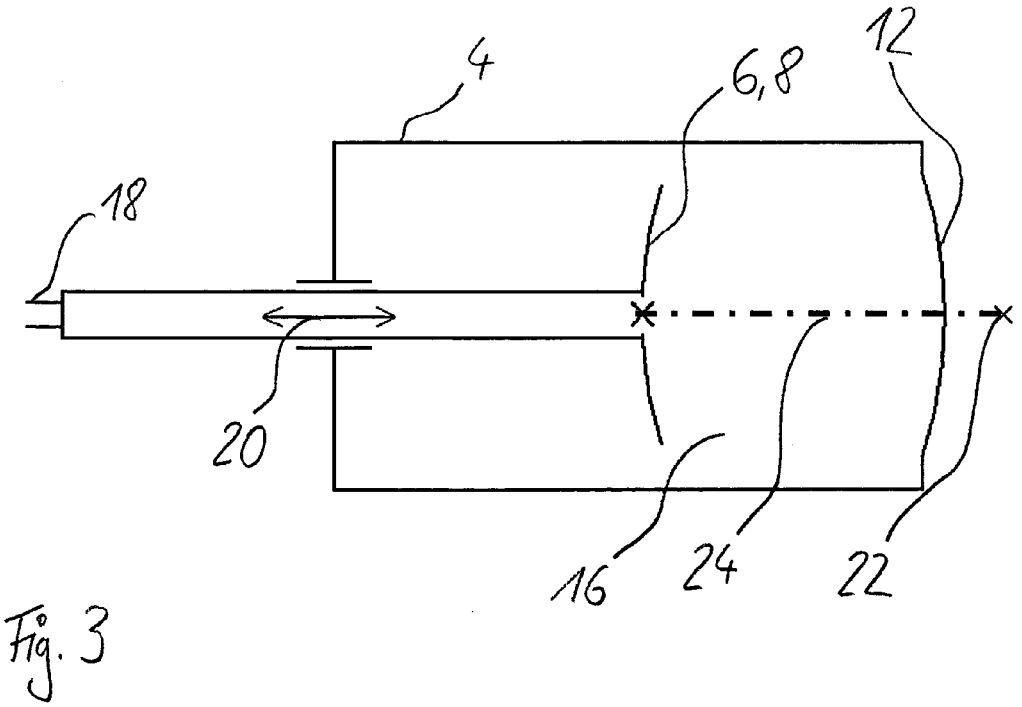
FIG. 3 shows a a side view of the device according to the invention in its third embodiment and FIG. 4 shows a side view of the device according to the invention in an embodiment with three-dimensional movement.

The shock waves can also be generated in another way, however, for example by an electromagnetic or piezoelectric shock wave generating device 6, which is depicted in the additional embodiments of the invention shown in FIG. 2 and FIG. 3, respectively.

In FIG. 2 a membrane of a flat coil forms the shock wave generating device 6. The generated shock waves are focussed via an acoustic lens 8. In the embodiment shown in FIG. 3 the shock waves are generated via piezoelements arranged in spherical form. The form of the shock wave generating device 6 forms the focusing device 8 in this context.

Figure 4:
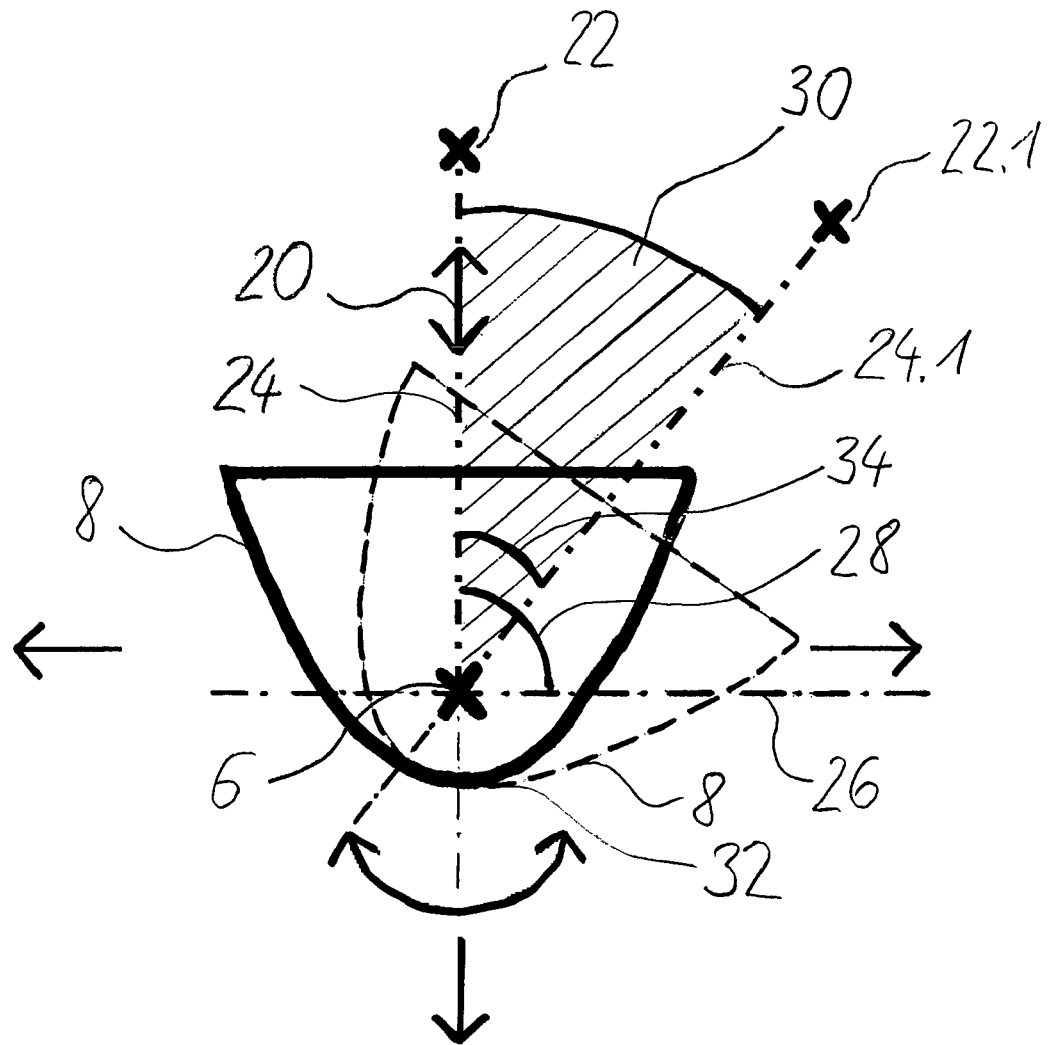

Various possibilities for moving or adjusting the device according to the invention are shown in schematic form in FIG. 4. An advantageous embodiment of the device according to the invention consists of a device in which the shock wave generating device 6 can be moved together with the focusing device 8 in the housing 4, which is not explicitly depicted in the figure, on a second axis 26, either simultaneously or consecutively, in addition to the movement 20 on the first axis 24. The shock wave focus 22 can thus be positioned in an advantageous manner in the region to be treated without moving either the patient or (in cases where they are required) a patient-positioning device or the therapy device. The second axis 26 and the first axis 24 form an angle 28 of preferably 90°.

In another embodiment, the shock wave generating device 6 together with the focusing device 8 is fastened to a point 32 in the housing 4 and elaborated in a movable manner such that the shock wave generating device 6 together with the focusing device 8 can be tilted at this point 32. The first axis 24 together with the first axis 24.1—in the tilted position of the shock wave generating device 6 and of the focusing device 8—a tilting angle 34; the shock wave generating device 6 together with the focusing device 8 are tilted by the dimension of this angle. The tilting angle 34 can be displayed to the user.

The main direction of shock wave propagation thus does not consist of only one direction but rather of various directions describing an area 30 shaped like the segment of a circle. The shock wave focus 22 is moved along the circumference of the area 30 shaped like a segment of a circle.

In addition, the shock wave generating device 6 can be moved together with the focusing device 8 in the direction of the coupling surface 12 and—either simultaneously or consecutively—be tilted in various directions or moved sidewise. With the movements described above, the shock wave focus 22 can be moved within a three-dimensional therapeutic area in the patient's body.

What is claimed is:

1. A device for the application of acoustic shock waves, the device comprising:
    an electrohydraulic shock wave generating device configured to generate the acoustic shock waves;
    a housing having a coupling surface configured to couple the acoustic shock waves into living tissue;
    a reflector located inside of the housing and surrounding the shock wave generating device to focus the acoustic shock waves to a shock wave treatment region, wherein the shock wave generating device and the reflector each linearly translate independent of and relative to one another and to the coupling surface in the housing along a first axis intersecting the coupling surface and along a second axis perpendicular to the first axis; and
    a fastening point within the housing pivotably supporting the reflector to tilt in a plurality directions for three-dimensional movement of the shock wave treatment region.

2. The device of claim 1, wherein the first axis extends through the shock wave generating device and the coupling surface to the shock wave treatment region.

3. The device of claim 1, wherein movement of the shock wave generating device and the reflector is manually driven.

4. The device of claim 1, further comprising a display providing a tilting angle of the reflector.

5. A device for the application of acoustic shock waves, the device comprising:
    an electrohydraulic shock wave generating device configured to generate the acoustic shock waves;
    a housing including:
        a first end having a coupling surface proximate thereto;
        a second end opposite the first end; and
        a membrane disposed at a location between the first end and the second end, the membrane and the second end forming a closed region disposed to receive a volume of conducting particles for generating a spark discharge to generate the acoustic shock waves, and the coupling surface being disposed to couple the acoustic shock waves into living tissue;
    reflector located inside of the housing and surrounding the shock wave generating device to focus the acoustic shock waves to a shock wave treatment region, wherein the shock wave generating device and the reflector each linearly translate in the housing along a plurality of axes independent of and relative to one another and to the membrane, wherein a first axis extends through the coupling surface and a second axis intersects the first axis; and
    a fastening point within the housing pivotably supporting the reflector to tilt in a plurality directions for three-dimensional movement of the shock wave treatment region.

6. The device of claim 5, wherein the second axis of the plurality of axes is perpendicular to the first axis.

7. The device of claim 5, further comprising an imaging apparatus configured to receive information indicative of a linear translation of the shock wave generating device and the reflector and of a tilting of the reflector and provide an image of the treatment region of a human or animal body based on the received information.

8. The device of claim 1, wherein the reflector is selected from the group consisting of a half-shell ellipsoidal reflector and paraboloidal reflector.

9. The device of claim 1, wherein movement of the shock wave generating device and the reflector is electromechanically driven.

10. The device of claim 1, wherein movement of the shock wave generating device and the reflector is hydraulically driven.

11. The device of claim 5, wherein the reflector is selected from the group consisting of a half-shell ellipsoidal reflector and paraboloidal reflector.

* * * * *